(12) United States Patent
Shammai et al.

(10) Patent No.: US 7,671,983 B2
(45) Date of Patent: Mar. 2, 2010

(54) METHOD AND APPARATUS FOR AN ADVANCED OPTICAL ANALYZER

(75) Inventors: Michael Shammai, Houston, TX (US);
Robert Gordon, The Woodlands, TX (US); Rocco DiFoggio, Houston, TX (US)

(73) Assignee: Baker Hughes Incorporated, Houston, TX (US)

( * ) Notice: Subject to any disclaimer, the term of this patent is extended or adjusted under 35 U.S.C. 154(b) by 419 days.

(21) Appl. No.: 10/837,475

(22) Filed: Apr. 30, 2004

(65) Prior Publication Data

US 2004/0218176 A1 Nov. 4, 2004

Related U.S. Application Data

(60) Provisional application No. 60/467,668, filed on May 2, 2003.

(51) Int. Cl.
*G01J 3/44* (2006.01)
(52) U.S. Cl. ...................................... 356/301
(58) Field of Classification Search ................ 356/301; 73/152, 16–17; 250/253, 256, 339.05
See application file for complete search history.

(56) References Cited

U.S. PATENT DOCUMENTS

| | | | |
|---|---|---|---|
| 3,448,611 A | | 6/1969 | Lebourg |
| 3,608,715 A * | | 9/1971 | Snyder et al. ................ 209/590 |
| 3,780,575 A * | | 12/1973 | Urbanosky, Harold J. .................. 73/152.26 |
| 3,859,851 A * | | 1/1975 | Urbanosky, Harold J. .................. 73/152.24 |
| 4,994,671 A * | | 2/1991 | Safinya et al. ................ 250/255 |
| 5,166,747 A | | 11/1992 | Schroeder et al. |
| 5,329,811 A * | | 7/1994 | Schultz et al. ............ 73/152.02 |
| 5,337,822 A * | | 8/1994 | Massie et al. ................ 166/264 |
| 5,734,098 A * | | 3/1998 | Kraus et al. ................. 73/61.62 |
| 5,741,962 A * | | 4/1998 | Birchak et al. ............ 73/152.16 |
| 5,859,430 A | | 1/1999 | Mullins et al. |
| 5,939,717 A * | | 8/1999 | Mullins ....................... 250/255 |
| 6,092,416 A | | 7/2000 | Halford et al. |
| 6,178,815 B1 | | 1/2001 | Felling et al. |
| 6,218,662 B1 * | | 4/2001 | Tchakarov et al. .......... 250/256 |
| 6,350,986 B1 | | 2/2002 | Mullins et al. |
| 6,378,364 B1 * | | 4/2002 | Pelletier et al. .......... 73/152.47 |

(Continued)

FOREIGN PATENT DOCUMENTS

| | | |
|---|---|---|
| EP | 0295923 A2 | 6/1988 |
| EP | 1205630 A2 | 5/2002 |

*Primary Examiner*—Tarifur R. Chowdhury
*Assistant Examiner*—Isiaka O Akanbi
(74) *Attorney, Agent, or Firm*—Madan & Sriram, P.C.

(57) ABSTRACT

The present invention provides a sample tank having a window for introduction of electromagnetic energy into the sample tank for analyzing a formation fluid sample down hole or at the surface without disturbing the sample. Near infrared, mid infrared and visible light analysis is performed on the sample to provide a downhole in situ or surface on site analysis of sample properties and contamination level. The onsite analysis comprises determination of gas oil ratio, API gravity and various other parameters which can be estimated by a trained neural network or chemometric equation. A flexural mechanical resonator is also provided to measure fluid density and viscosity from which additional parameters can be estimated by a trained neural network or chemometric equation. The sample tank is pressurized to obviate adverse pressure drop or other effects of diverting a small sample.

34 Claims, 7 Drawing Sheets

U.S. PATENT DOCUMENTS

| | | | |
|---|---|---|---|
| 6,437,326 B1 * | 8/2002 | Yamate et al. | 250/269.1 |
| 6,683,681 B2 * | 1/2004 | DiFoggio et al. | 356/128 |
| 2002/0129936 A1 | 9/2002 | Cernosek | |
| 2003/0033866 A1 | 2/2003 | Diakonov et al. | |
| 2003/0066646 A1 | 4/2003 | Shammai et al. | |
| 2004/0089448 A1 | 5/2004 | DiFoggio | |

* cited by examiner

METHOD AND APPARATUS FOR AN ADVANCED OPTICAL ANALYZER

CROSS REFERENCE TO RELATED APPLICATIONS

This patent application claims priority from U.S. Provisional Patent Application Ser. No. 60/467,668 entitled "A Method and Apparatus for an Advanced Optical Cylinder" by M. Shammai et al. filed on May 2, 2003.

BACKGROUND OF THE INVENTION

1. Field of the Invention

The present invention relates generally to the field of downhole sampling analysis and in particular to a sample tank having a window or an internal light source for introduction of electromagnetic energy into a confined fluid sample. There response to the introduction of electromagnetic energy into the tank is used to perform non-invasive analysis of a sample in the tank without opening the tank or otherwise disturbing the sample.

2. Summary of the Related Art

Earth formation fluids in a hydrocarbon producing well typically comprise a mixture of oil, gas, and water. The pressure, temperature and volume of formation fluids control the phase relation of these constituents. In a subsurface formation, high well fluid pressures often entrain gas within the oil above the bubble point pressure. When the pressure is reduced, the entrained or dissolved gaseous compounds separate from the liquid phase sample. The accurate measurement of pressure, temperature, and formation fluid composition from a particular well affects the commercial viability for producing fluids available from the well. The data also provides information regarding procedures for maximizing the completion and production of the respective hydrocarbon reservoir.

Certain techniques analyze the well fluids downhole in the well bore. U.S. Pat. No. 6,467,544 to Brown, et al. describes a sample chamber having a slidably disposed piston to define a sample cavity on one side of the piston and a buffer cavity on the other side of the piston. U.S. Pat. No. 5,361,839 to Griffith et al. (1993) disclosed a transducer for generating an output representative of fluid sample characteristics downhole in a wellbore. U.S. Pat. No. 5,329,811 to Schultz et al. (1994) disclosed an apparatus and method for assessing pressure and volume data for a downhole well fluid sample.

Other techniques capture a well fluid sample for retrieval to the surface. U.S. Pat. No. 4,583,595 to Czenichow et al. (1986) disclosed a piston actuated mechanism for capturing a well fluid sample. U.S. Pat. No. 4,721,157 to Berzin (1988) disclosed a shifting valve sleeve for capturing a well fluid sample in a chamber. U.S. Pat. No. 4,766,955 to Petermann (1988) disclosed a piston engaged with a control valve for capturing a well fluid sample, and U.S. Pat. No. 4,903,765 to Zunkel (1990) disclosed a time-delayed well fluid sampler. U.S. Pat. No. 5,009,100 to Gruber et al. (1991) disclosed a wireline sampler for collecting a well fluid sample from a selected wellbore depth. U.S. Pat. No. 5,240,072 to Schultz et al. (1993) disclosed a multiple sample annulus pressure responsive sampler for permitting well fluid sample collection at different time and depth intervals, and U.S. Pat. No. 5,322,120 to Be et al. (1994) disclosed an electrically actuated hydraulic system for collecting well fluid samples deep in a wellbore.

Temperatures downhole in a deep wellbore often exceed 300 degrees F. When a hot formation fluid sample is retrieved to the surface at 70 degrees F., the resulting drop in temperature causes the formation fluid sample to contract. If the volume of the sample is unchanged, such contraction substantially reduces the sample pressure. A pressure drop causes changes in the situ formation fluid parameters, and can permit phase separation between liquids and gases entrained within the formation fluid sample. Phase separation significantly changes the formation fluid characteristics, and reduces the ability to evaluate the actual properties of the formation fluid.

To overcome this limitation, various techniques have been developed to maintain pressure of the formation fluid sample. U.S. Pat. No. 5,337,822 to Massie et al. (1994) pressurized a formation fluid sample with a hydraulically driven piston powered by a high-pressure gas. Similarly, U.S. Pat. No. 5,662,166 to Shammai (1997) used a pressurized gas to charge the formation fluid sample. U.S. Pat. No. 5,303,775 (1994) and U.S. Pat. No. 5,377,755 (1995) to Michaels et al. disclosed a bi-directional, positive displacement pump for increasing the formation fluid sample pressure above the bubble point so that subsequent cooling did not reduce the fluid pressure below the bubble point.

Typically, sample tanks are transported to laboratories for analysis for determination of formation fluid properties based on the sample. The samples typically have to be transferred to a transportation tank, thus risking sample damage and spoilage due to pressure loss and formation of bubbles or asphaltene precipitation within the sample. Moreover, even if the sample is transferred successfully to the laboratory, it typically takes weeks or months to receive a full laboratory analysis of the sample. Thus there is a need for a rapid sample analysis system that provides accurate results and eliminates the risk of sample spoilage.

SUMMARY OF THE INVENTION

The present invention addresses the shortcomings of the related art described above. The present invention provides a downhole sample tank having at least one window for introduction of visible, near-infrared (NIR), mid-infrared (MIR) and other electromagnetic energy into the tank for samples collected in the sample tank downhole from an earth boring or well bore. The window is made of sapphire or another material capable of allowing electromagnetic energy to pass through the window. The entire sample tank can be made of sapphire or another material capable of allowing electromagnetic energy to pass another material enabling visual inspection or analysis of the sample inside the sample chamber. The present invention also provides interior NIR/MIR light sources and sensors that communicate from inside of the sample tank via electronic data signals. NIR, MIR and visible light analysis (transmittance, reflectance, and absorption) is performed on the sample via the window to provide a non-invasive analysis of sample properties and contamination level. A single window transmits light reflected off a reflective surface inside of the sample tank to obtain transmittance data through a single window.

The surface and down hole analysis comprises determination of gas oil ratio, API gravity and various other physical parameters associated with the sample which can be calculated or estimated by a trained neural network or chemometric equation. A flexural mechanical or piezoelectric resonator is also provided to estimate fluid density and viscosity from which additional parameters can be estimated by a trained neural network, non linear least squares fit, chemometric equation or other soft modeling techniques well appreciated in the art. The sample tank is over pressurized above the bubble point for the sample to prevent adverse pressure drop.

When very high pressures are desired the sample is supercharged with a pressurization gas charge. The down hole sample tank comprises a housing having a hollow interior and at least one window, a fiber optics lead, optical conduit or internal light source or sensor for introduction and detection of electromagnetic energy into the sample tank.

BRIEF DESCRIPTION OF THE FIGURES

For detailed understanding of the present invention, references should be made to the following detailed description of the preferred embodiment, taken in conjunction with the accompanying drawings, in which like elements have been given like numerals, wherein.

DETAILED DESCRIPTION OF AN EXEMPLARY EMBODIMENT

Figure 1:
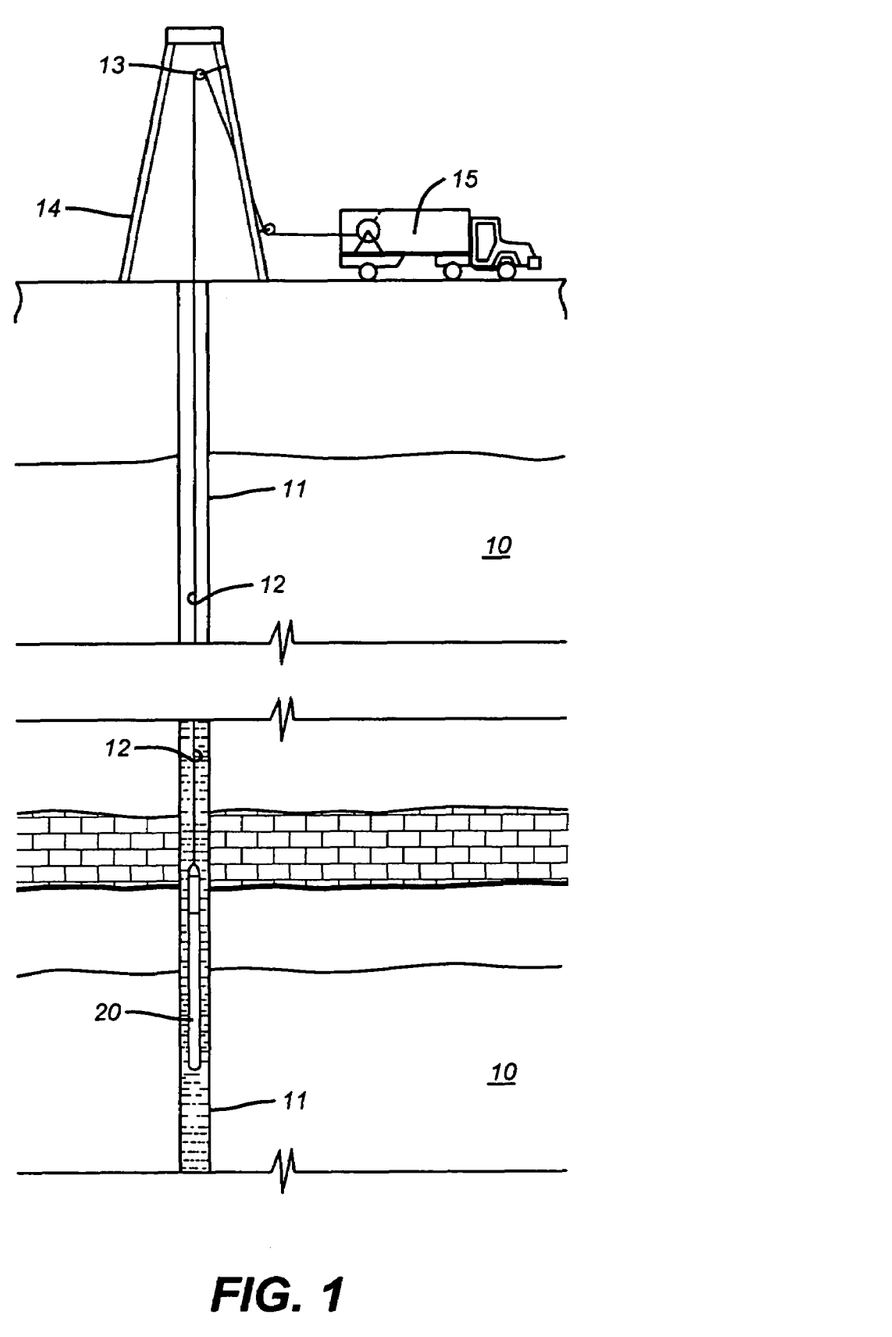
FIG. 1 is a schematic earth section illustrating the invention operating environment.

FIG. 1 schematically represents a cross-section of earth 10 along the length of a wellbore penetration 11. Usually, the wellbore will be at least partially filled with a mixture of liquids including water, drilling fluid, and formation fluids that are indigenous to the earth formations penetrated by the wellbore. Hereinafter, such fluid mixtures are referred to as "wellbore fluids". The term "formation fluid" hereinafter refers to a specific formation fluid exclusive of any substantial mixture or contamination by fluids not naturally present in the specific formation.

Suspended within the wellbore 11 at the bottom end of a wireline 12 is a formation fluid sampling tool 20. The wireline 12 is often carried over a pulley 13 supported by a derrick 14. Wireline deployment and retrieval is performed by a powered winch carried by a service truck 15, for example.

Figure 2:
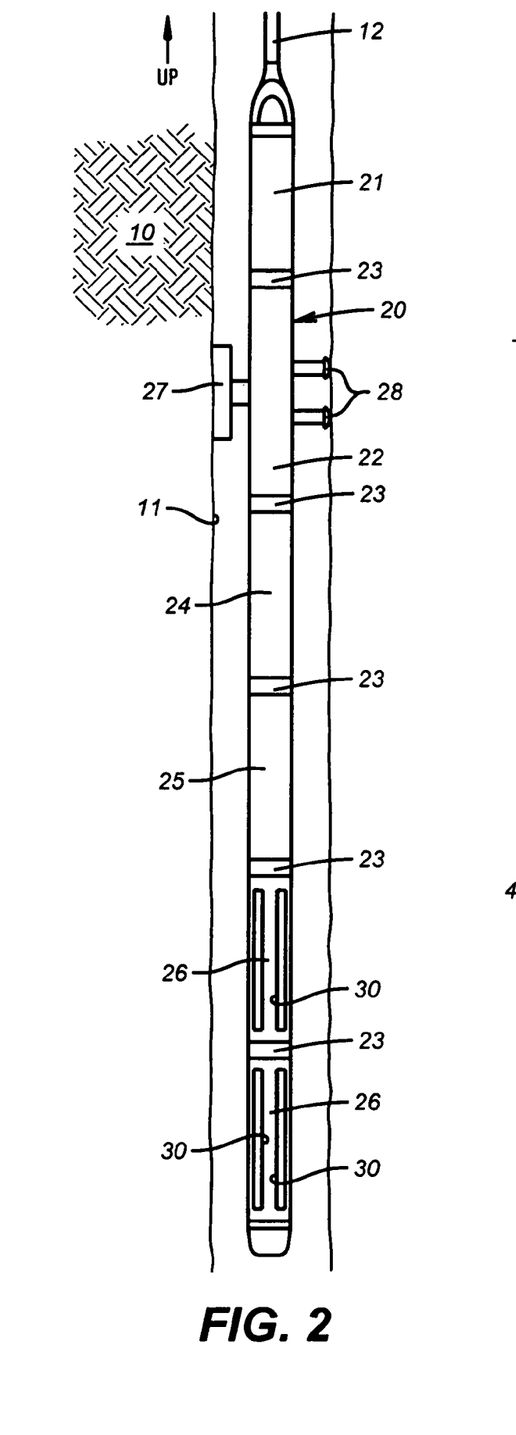
FIG. 2 is a schematic of the invention in operative assembly with cooperatively supporting tools.
Figure 3:
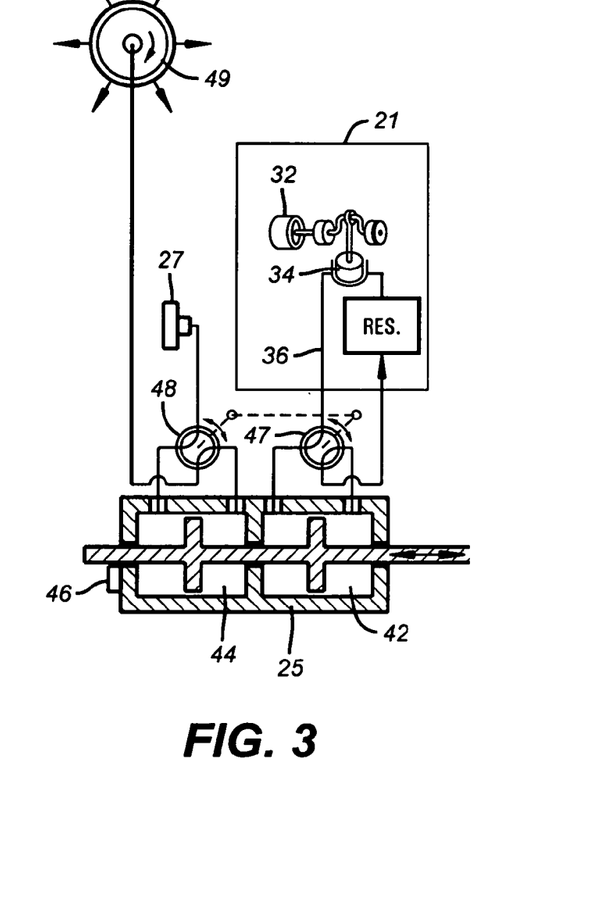
FIG. 3 is a schematic of a representative formation fluid extraction and delivery system.

Pursuant to the present invention, an exemplary embodiment of a sampling tool 20 is schematically illustrated by FIG. 2. In the present example, the sampling tools comprise a serial assembly of several tool segments that are joined end-to-end by the threaded sleeves of mutual compression unions 23. An assembly of tool segments appropriate for the present invention may include a hydraulic power unit 21 and a formation fluid extractor 23. Below the extractor 23, a large displacement volume motor/pump unit 24 is provided for line purging. Below the large volume pump is a similar motor/pump unit 25 having a smaller displacement volume that is quantitatively monitored as described more expansively with respect to FIG. 3. Ordinarily, one or more sample tank magazine sections 26 are assembled below the small volume pump. Each magazine section 26 may have three or more fluid sample tanks 30.

The formation fluid extractor 22 comprises an extensible suction probe 27 that is opposed by bore wall feet 28. Both, the suction probe 27 and the opposing feet 28 are hydraulically extensible to firmly engage the wellbore walls. Construction and operational details of the fluid extraction tool 22 are more expansively described by U.S. Pat. No. 5,303,775, the specification of which is incorporated herewith.

Figure 4:
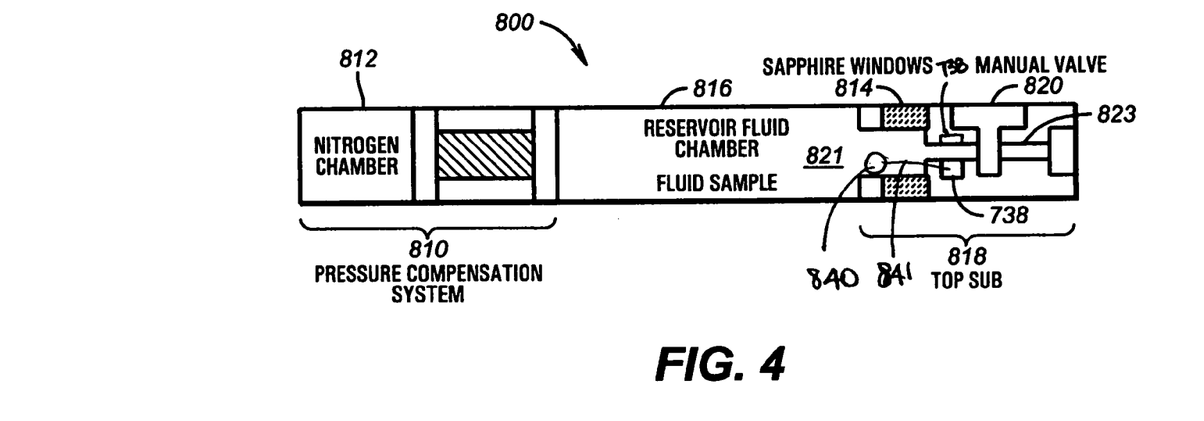
FIG. 4 is an illustration of a preferred sample chamber and analysis top sub.

Turning now to FIG. 4, in an exemplary embodiment of the present invention, an advanced optical analyzer (AOA) 800 is provided which comprises a sample tank 816 having an integral analytical top sub 818. The sample 821 in the sample tank can be pressurized by the pressurized compensation system which comprises a pressure compensation system 810, having a nitrogen pressure chamber 812. The nitrogen pressure is available when very high pressure is desired. Pressure is applied sufficient to keep a down hole fluid sample 821 in chamber 816 above the bubble point pressure and above the pressure at which asphaltenes precipitate out of the sample. The AOA is also suitable for downhole capture, pressurization and analysis of gas captured in a sample 821 confined in chamber 816.

The present example of the AOA top sub 818 provides one or more optical conduits, which in this example are high-pressure sapphire windows 814 for ingress and egress of electromagnetic energy into the analysis chamber 800 optical analysis of parameters of interest for formation fluid sample 821. The entire AOA including the analysis chamber can be made of sapphire or another material which enables electromagnetic energy to pass through the material, thereby enabling visual inspection and noninvasive spectral and other analysis of the contents of the AOA, including the sample chamber. Optical conduits other than a sapphire window are acceptable. An analysis module 738 comprising a light source, light sensor and processor is provided which can be used for analysis of the sample 821 down hole or at the surface. Analysis module 738 is in contact with the sample 821 in sample region 823 for transmission and reception of NIR/MIR light into and through the sample in region 823. The light reflected, fluoresced and transmitted NIR/MIR light is analyzed for transmittance, reflectance and luminance by the processor in analysis module 738. A flexural mechanical resonator 840 connected to analysis module 738 by communication line 741 is also provided to determine fluid viscosity, density and other parameters of interest for the fluid sample using soft modeling techniques.

Figure 5:
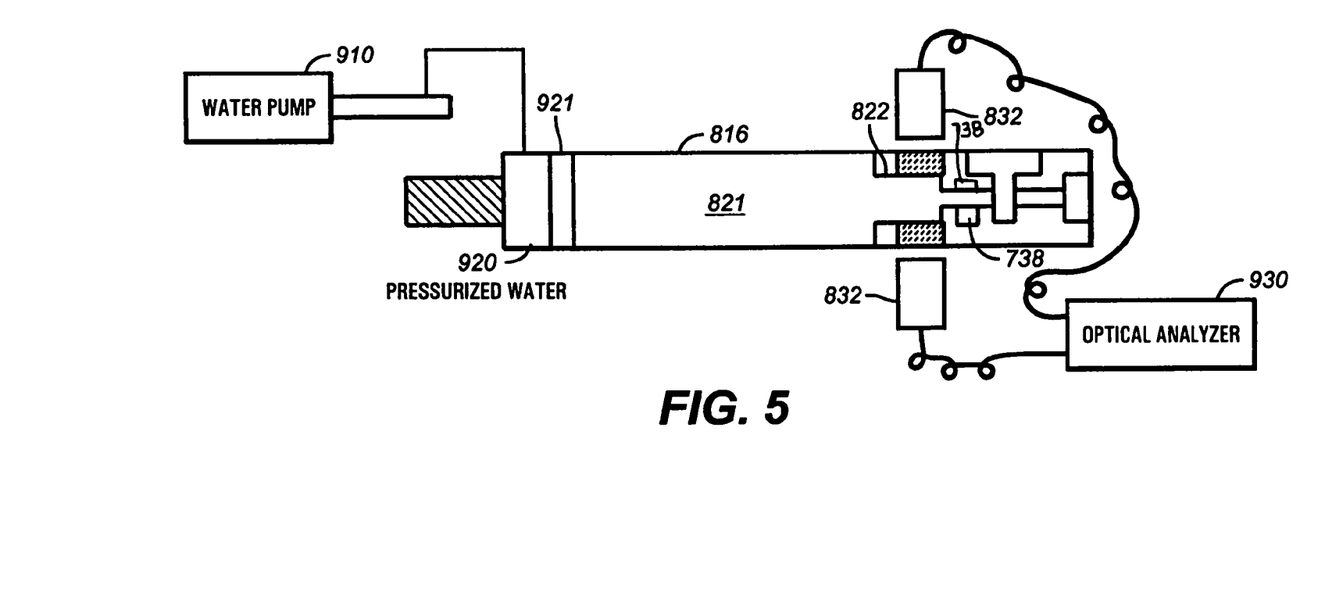
FIG. 5 is an illustration of an alternative embodiment having a water pump to pressurize a sample for analysis by an external unit.

In surface operations, as shown in FIG. 5, the AOA 800 is removed from a sample tank carrier and the sample 821 pressure is stabilized by pumping pressurized water 920 behind the piston 921 using pump 910. At this time the nitrogen can be released and the nitrogen chamber can be detached from the sample chamber. An external optical analyzer 930 or analysis module 738 comprising an NIR/MIR ultraviolet or visible light source and spectrometers provided for surfaces or down hole non-invasive analysis. The optical analyzer 930 is connected to a NIR/MIR light source 832 and a NIR/MIR light sensor 833 for analysis of light transmittance, fluorescence and total attenuated reflectance. That is, without disturbing the fluid sample or requiring transferring the sample to another Department of Transportation (DOT) approved chamber for transport to an off-site laboratory for analysis.

The external optical analyzer 930 or internal analyzer 738 in the current example uses wavelength ranges from 1500 nm to 2000 nm to scan the fluid sample to determine or estimate through soft modeling techniques, parameters of interest, such as sample contamination percentage, gas oil ratio (GOR), density and asphaltene deposition pressure. A tunable diode laser and a Raman spectrometer are also provided in analysis module 738 for spectral analysis of the fluid sample. Each of the light sources and sensors are located inside of the sample tank 816 or communicate with the interior of the sample tank via the optical window 814 or an equivalent optical conduit providing data or electromagnetic energy ingress and egress to the interior of the sample tank and the sample retained therein.

Figure 6:
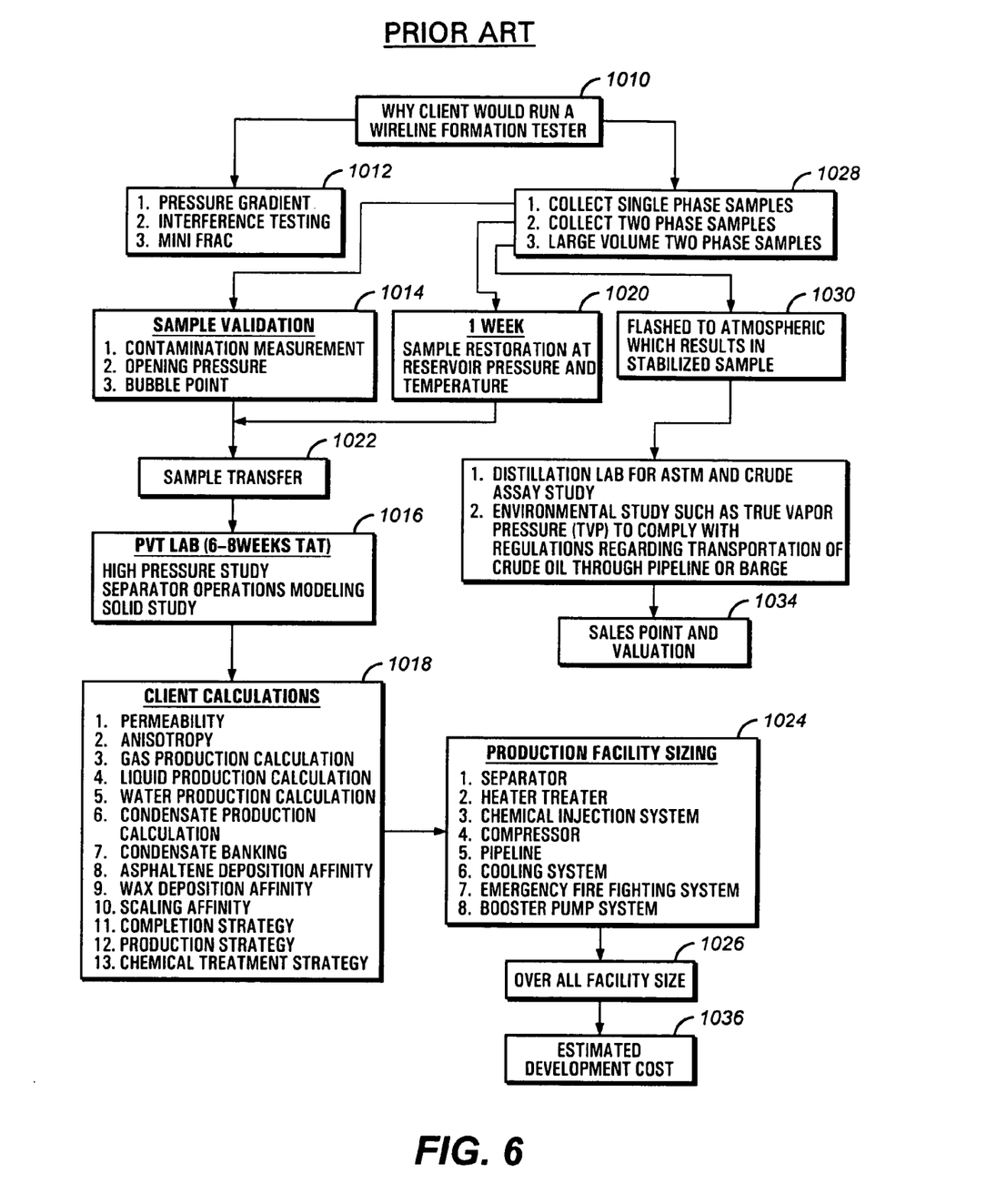
FIG. 6 is an illustration of a common current analysis procedure.
Figure 7:
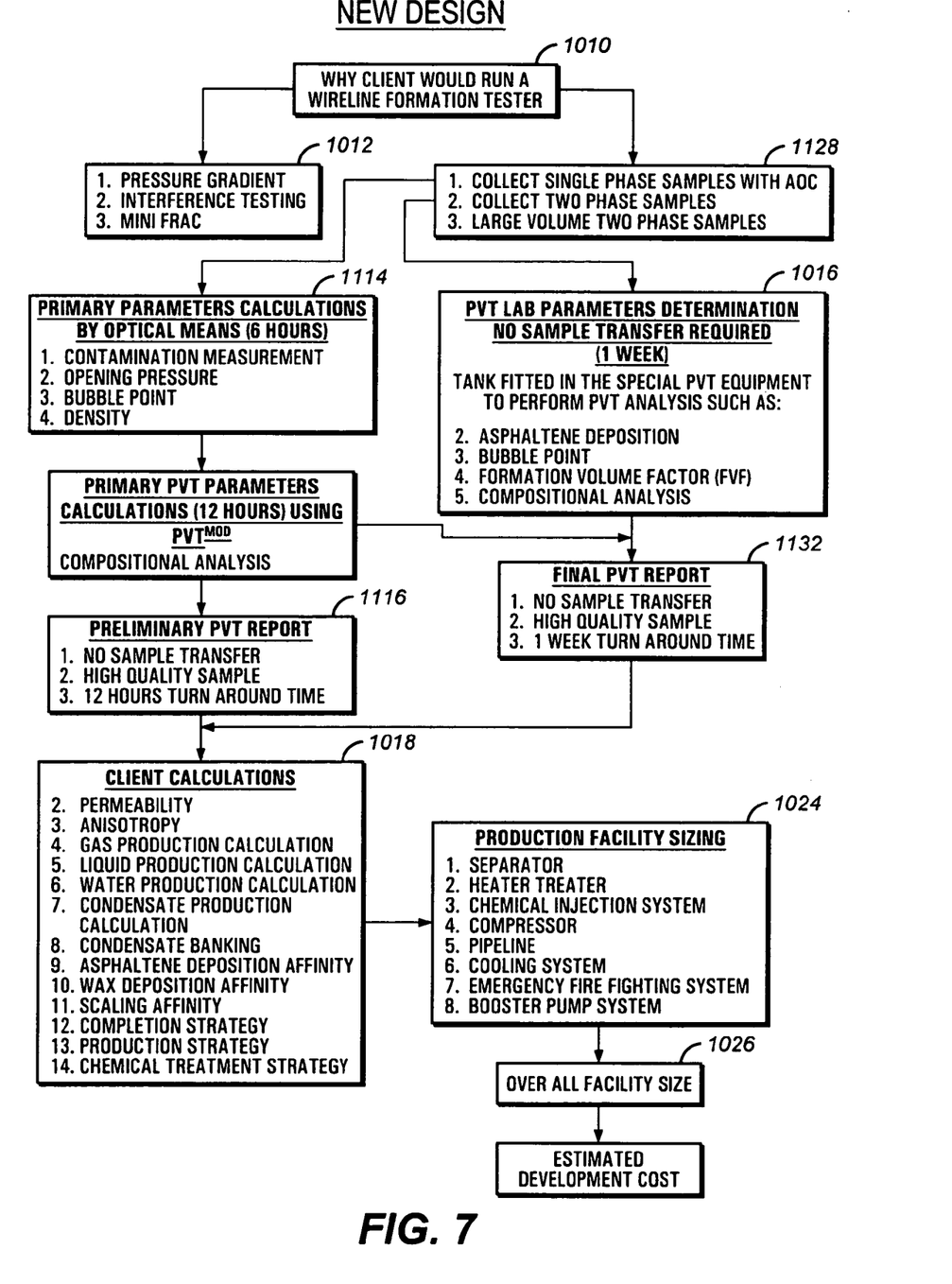
FIG. 7 is an illustration of the new improved procedure provided by the present invention.

The analysis module 738 is attached as an integral part of the sample tank in the AOA prior to going down hole. The analysis module is used to perform NIR/MIR and other analysis described herein downhole during a run or at the surface upon completion of a sampling run downhole. Some of the numerous advantages of the AOA of the present invention are shown by comparison to FIG. 6, a prior art system and FIG. 7, the new method and apparatus design provided by the AOA of the present invention. Note that in FIG. 7 that a primary parameter calculation by optical techniques 1114 is available immediately or in less than six hours and a final PVT report 1132 in less than a week or less rather than six to eight weeks as shown in FIG. 6 for the prior art system. An advantage for the disclosed method and apparatus is that no sample transfer is required, as non-invasive surface or down hole equipment in both the analysis module 738 and external equipment 830 perform PVT and spectral analysis to determine asphaltene deposition, bubble point, formation volume factor, compositional analysis and additional analysis described herein.

Figure 8:
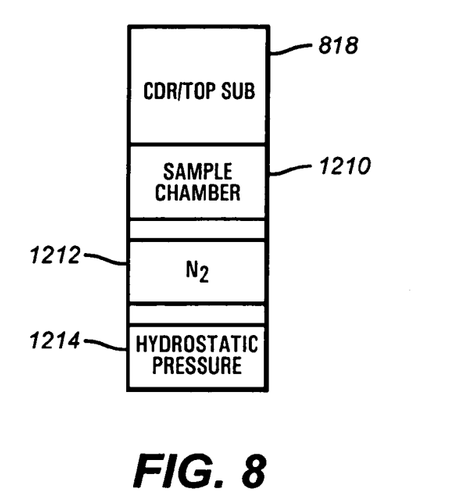
FIG. 8 is an illustration of an alternative embodiment.

Turning now to FIG. 8 an alternative embodiment of the present invention is presented showing top sub 818 containing analysis module 738 attached to sample chamber 1210 pressurized by nitrogen ($N_2$) 1212 and hydrostatic pressure 1214 while down hole. Thus, the present invention can perform sampling and sample analysis while down hole or at the surface as shown in FIGS. 4, 5 and 8.

Figure 9:
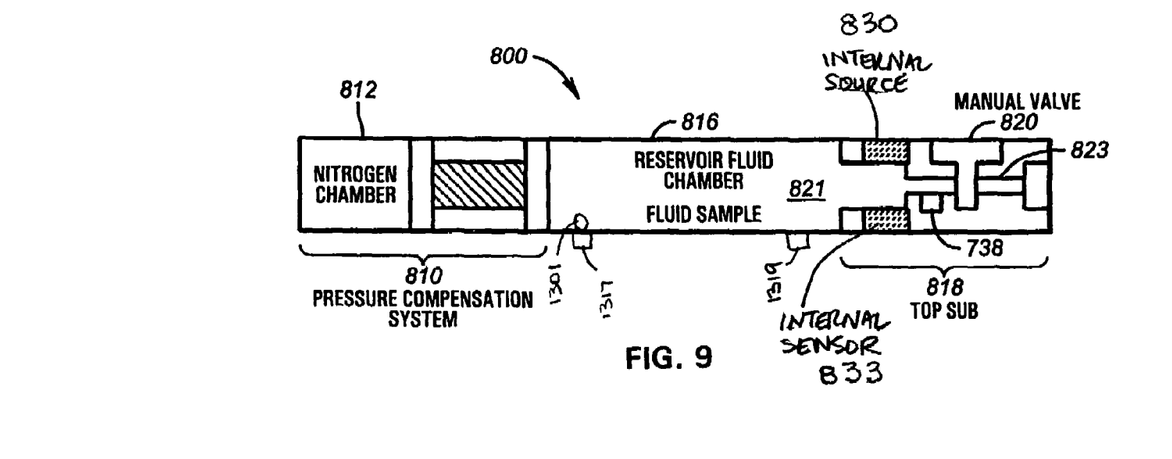
FIG. 9 is an illustration of an alternative embodiment having an internal light source and sensor.

Turning now to FIG. 9, an alternative embodiment is shown wherein an internal light source 830 and an internal sensor 833 are provided for noninvasive optical analysis of the sample 821. The internal processor embedded in analysis module 738, an external analyzer 930 or a surface analyzer in surface truck 15 process the optical data to determine a parameter of interest for the fluid sample 821. As shown in FIG. 9, to determine viscosity a ball 1301 is held in place by magnet 1317 and released in fluid sample contained in fluid sample chamber 1210. The ball is sensed by magnetic sensor 1319 upon arrival at point 1319. The processor determines the amount of time it takes for ball 1301 to travel between point 1317 and point 1319 and determines the fluid viscosity therefrom.

Figure 10:
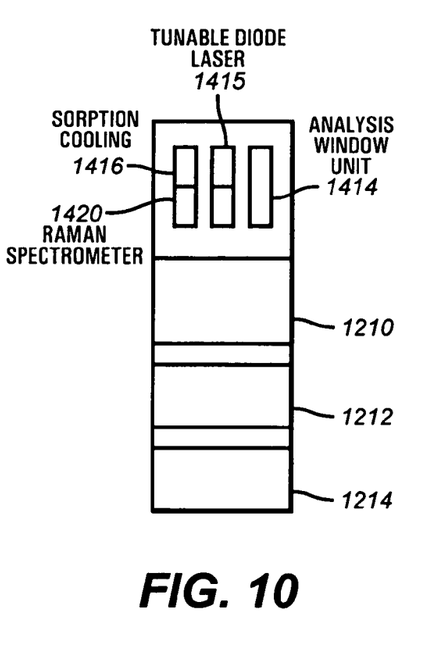
FIG. 10 is an illustration of an alternative embodiment having a single window and a reflective surface for return of electromagnetic radiation.

As shown in FIG. 10, analysis window unit comprises analysis module 738, tunable diode laser spectrometer 1415 or other optical spectrometer and sorption cooling unit 1416. Sorption cooling unit 1416 is described in co-owned patent application Ser. No. 09/756,764 filed on Jan. 8, 2001 entitled Downhole Sorption Cooling in Wireline Logging and Monitoring While Drilling" by Rocco DiFoggio, incorporated herein by reference in its entirety.

The tunable diode laser 1415 spectrometer enable the ultra high resolution spectroscopy downhole or at the surface. Sorption cooling unit 1416 cools the tunable diode laser as necessary to obviate the adverse affects of downhole temperatures.

Figure 11:
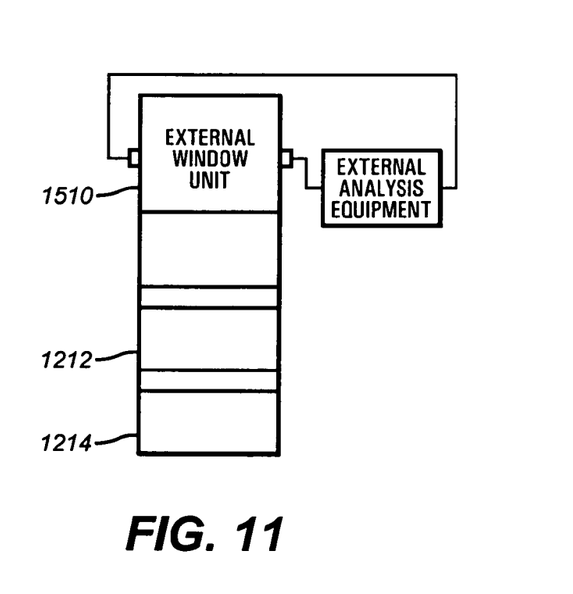
FIG. 11 is an illustration of another alternative embodiment using a Raman spectrometer.

Turning now the FIG. 11, an alternative embodiment of the present invention is shown providing an external window unit 1510 for surface or downhole attachment of analysis equipment such as gas chromatographs or other analysis equipment.

Figure 12:
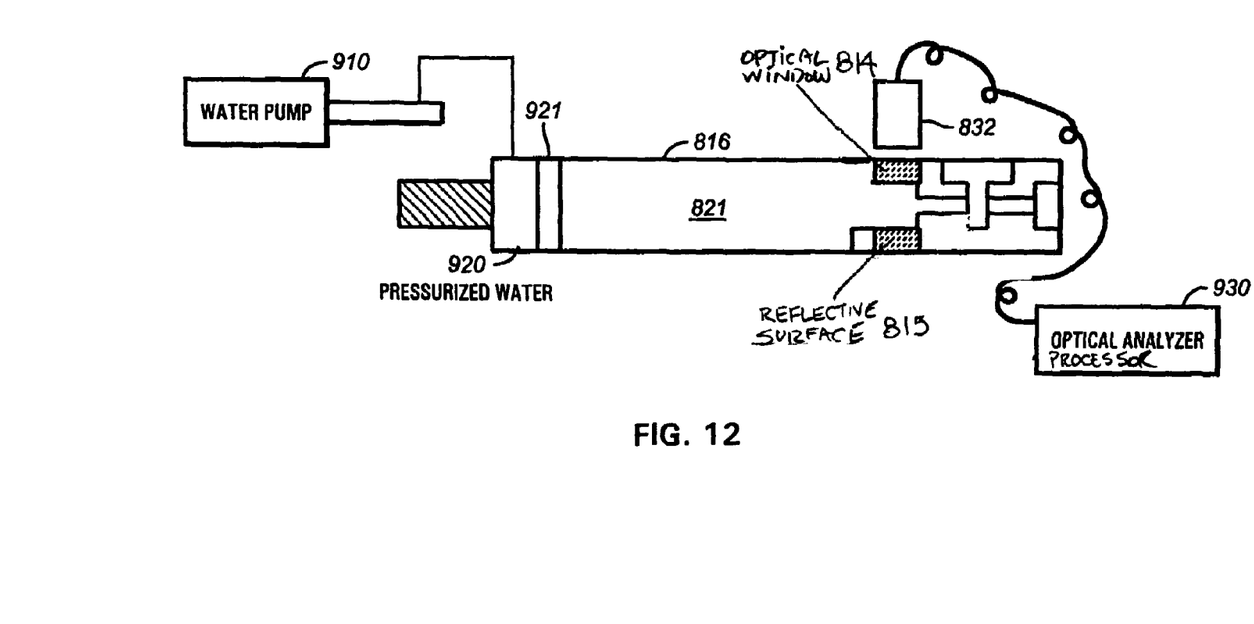
FIG. 12 is an illustration of another alternative embodiment using an external analysis equipment and at least one optical window.

FIG. 12 is an illustration of an alternative embodiment having a single optical conduit 814, in this example a sapphire window 814 for ingress and egress of electromagnetic energy into and out of the sample chamber 816. Light from light source/sensor 832 enter the sample chamber 816 through single optical window 814. The light travels through the sample and bounces off of reflective surface 815. Thus, the round trip transmittance can determined from reflection and return of electromagnetic energy. Transmittance is determined for round trip travel of the light through the optical conduit, through the sample, reflected off of the reflective surface, returned through the sample and back through the optical conduit for measurement. Attenuated total reflectance and fluorescence response data are also sensed but do not use the reflective surface 815. The data is processed by processor in analysis module 738, internal analyzer/processor 930 or surface truck/controller/processor 15.

In another embodiment, the method and apparatus of the present invention is implemented as a set computer executable of instructions on a computer readable medium, comprising ROM, RAM, CD-ROM, Flash RAM or any other computer readable medium, now known or unknown that when executed cause a computer to implement the functions of the present invention.

While the foregoing disclosure is directed to the preferred embodiments of the invention various modifications will be apparent to those skilled in the art. It is intended that all variations within the scope of the appended claims be embraced by the foregoing disclosure. Examples of the more important features of the invention have been summarized rather broadly in order that the detailed description thereof that follows may be better understood, and in order that the contributions to the art may be appreciated. There are, of course, additional features of the invention that will be described hereinafter and which will form the subject of the claims appended hereto.

The invention claimed is:

1. An apparatus configured to estimate an initial property of a downhole fluid comprising:
    a chamber that contains the fluid retrieved from a formation;
    a first window formed in the chamber,
    a second window formed in the chamber;
    a surface source configured to connect with the first window and to emit electromagnetic radiation from outside the chamber to the fluid after the chamber has been retrieved to a surface location to estimate the initial property; and
    a surface sensor configured to connect with the second window after the chamber has been retrieved to the surface location and to detect electromagnetic radiation that egresses through the second window.

2. The apparatus of claim 1, further comprising:
    an optical analyzer associated with the chamber in electromagnetic communication with the fluid.

3. The apparatus of claim 2, wherein the optical analyzer is one of the set consisting of an optical spectrometer, an absorption spectrometer and a Raman spectrometer.

4. The apparatus of claim 1, wherein the chamber comprises sapphire.

5. The apparatus of claim 1, wherein the chamber further comprises at least one of the set of a closed chamber and an open chamber.

6. The apparatus of claim 1, further comprising a piezoelectric resonator configured to estimate a second property of the fluid.

7. The apparatus of claim 1, further comprising:
a processor configured to perform a soft modeling technique for estimating a second property for the fluid from the initial property of the fluid.

8. The apparatus of claim 1, wherein the first window and the second window are the same window that is configured for ingress and egress of electromagnetic energy into and out of the chamber.

9. The apparatus of claim 1, further comprising:
a reflector positioned in the chamber reflecting electromagnetic radiation, the reflector being configured to reflect electromagnetic radiation that enters the chamber through the first window back through the first window.

10. The apparatus of claim 1, further comprising a downhole tool containing the chamber, and wherein the chamber is configured to confine the fluid and is removable from the downhole tool.

11. An apparatus configured to estimate property for a downhole fluid comprising:
a sample tank carrier;
a chamber containing the fluid and being removably coupled to the sample tank carrier;
a pressure compensation device configured to control pressure in the chamber at least until the sample tank carrier is at a surface location;
a surface source configured to connect with the first window and to emit electromagnetic radiation from outside the chamber to the fluid after the chamber has been retrieved to the surface location to estimate the initial property;
a surface sensor configured to connect with the second window after the chamber has been retrieved to the surface location and to detect electromagnetic radiation that egresses through the second window; and
a processor configured to estimate the property based on a reading from the surface sensor.

12. The apparatus of claim 11, further comprising:
an optical analyzer comprising at least one of the set consisting of an optical spectrometer, an absorption spectrometer and a Raman spectrometer.

13. The apparatus of claim 11, further comprising:
a piezoelectric resonator configured to estimate a second property of the fluid.

14. The apparatus of claim 11, wherein the processor is configured to perform a soft modeling technique for estimating a second property of the fluid from the initial property of the fluid.

15. The apparatus of claim 11, further comprising:
a reflector positioned in the chamber reflecting electromagnetic radiation, the reflector being configured to reflect electromagnetic radiation that enters the chamber through the first window back through the first window.

16. The apparatus of claim 11, further comprising a downhole tool containing the chamber, wherein the chamber is configured to confine the fluid and is removable from the downhole tool, and wherein the pressure compensation device is configured to maintain a pressure in the chamber at one of: (i) above a bubble point pressure, and (ii) above a pressure at which asphaltenes precipitate out of the fluid.

17. A system configured to estimate an initial property of a downhole fluid comprising:
a downhole tool;
a chamber removably connected to the downhole tool, the chamber configured to contain the fluid downhole and a first window that allows passage of an electromagnetic radiation from outside the chamber to the fluid;
a pressure compensation device maintaining a pressure in the chamber at least above a bubble point pressure of the fluid at least until the downhole tool is at a surface location;
a surface source configured to connect with the first window and to emit electromagnetic radiation into the chamber after the chamber has been retrieved to the surface location; and
a surface sensor configured to connect with the second window after the chamber has been retrieved to the surface location and to detect electromagnetic radiation that egresses through the second window to estimate the initial property.

18. The system of claim 17, further comprising:
an optical analyzer in electromagnetic communication with the fluid.

19. The system of claim 18, wherein the optical analyzer is at least one of the set consisting of an optical spectrometer, an absorbance spectrometer and a Raman spectrometer.

20. The system of claim 17, wherein the first and second windows comprise sapphire.

21. The system of claim 17, further comprising:
a piezoelectric resonator for estimating a second property of the fluid.

22. The system of claim 17, further comprising:
a processor configured to perform a soft modeling technique for estimating a second property of the fluid from the initial property of the fluid.

23. The system of claim 17, wherein the first and second windows are made of a material that allows transmission of electromagnetic energy through the material.

24. The system of claim 17, further comprising:
a reflector positioned in the chamber and configured to reflect electromagnetic radiation that enters the chamber through the first window back through the first window.

25. The system of claim 17, wherein the chamber is configured to confine the fluid.

26. A method for estimating an initial property of a fluid downhole comprising:
containing a fluid downhole in a chamber;
passing electromagnetic energy from outside the chamber via a first window on the chamber into the fluid after the chamber has been retrieved to a surface location using a surface energy source; and
measuring electromagnetic radiation from the fluid that egresses through a second window on the chamber using a surface sensor after the chamber has been retrieved to the surface location to estimate the initial property.

27. The method of claim 26, wherein the first and second windows comprise sapphire.

28. The method of claim 27, wherein the analyzing comprises analyzing spectra of the electromagnetic radiation from the fluid using at least one of the set consisting of an optical spectrometer, an absorption spectrometer and a Raman spectrometer.

29. The method of claim 27, wherein the analyzing comprises analyzing light that passes through the second window.

30. The method of claim 26, wherein analyzing further comprises:

estimating a second property of the fluid using a piezoelectric resonator.

31. The method of claim 26, further comprising:
performing a soft modeling technique on the initial property of the fluid for estimating a second property of the fluid.

32. The method of claim 26, wherein the first and second windows are made of a material that allows transmission of electromagnetic energy through the material.

33. The method of claim 26, further comprising:
reflecting electromagnetic radiation that entered the chamber through the first window back through the first window using a reflector positioned in the chamber.

34. The method of claim 26, further comprising conveying the chamber into a wellbore using a downhole tool, confining the fluid in the chamber, and removing the chamber from the downhole tool.

* * * * *